United States Patent [19]

Crossley

[11] Patent Number: 4,547,510

[45] Date of Patent: Oct. 15, 1985

[54] 8-BENZYLIDENE-5,6,7,8-TETRAHY-DROQUINOLINE DERIVATIVES

[75] Inventor: Roger Crossley, Reading, England

[73] Assignee: John Wyeth & Brother Ltd., Maidenhead, England

[21] Appl. No.: 599,388

[22] Filed: Apr. 12, 1984

[30] Foreign Application Priority Data

Apr. 28, 1983 [GB] United Kingdom ............... 8311652

[51] Int. Cl.[4] ..................... A61K 31/47; C07D 215/04
[52] U.S. Cl. .................................. 514/311; 546/152; 546/174
[58] Field of Search ................. 546/152, 174; 424/258

[56] References Cited

U.S. PATENT DOCUMENTS 4,031,102  6/1977  Curran .................. 260/294.8 C

OTHER PUBLICATIONS

Burger "Medicinal Chemistry" 2nd Edition, p. 42.
Epsztajn Chemical Abstracts 71:112773b.
Arch. Pharm. (Weinheim): (a) Lodde 312, pp. 940–950 (1979), (b) Zymalkowski, 303 pp. 667–675, (1970).
Arch. Pharm. (Weinheim) Dammertz 313 pp. 826–832, (1980).

Primary Examiner—Donald G. Daus
Assistant Examiner—Robert Benson

Attorney, Agent, or Firm—Arthur G. Seifert

[57] ABSTRACT

This invention concerns compounds of formula

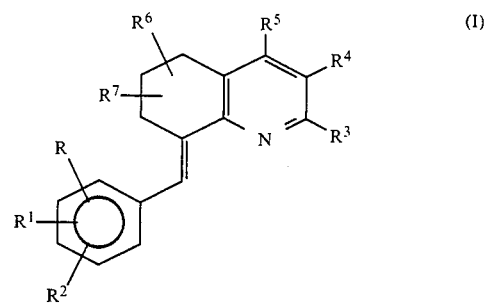

and acid addition salts thereof, wherein
R represents lower alkoxy, alkanoyloxy of 2 to 7 carbon atoms or hydroxy;
$R^1$ and $R^2$ independently represent hydrogen, lower alkoxy, alkanoyloxy of 2 to 7 carbon atoms, hydroxy or lower alkyl;
$R^3$, $R^4$ and $R^5$ each represent hydrogen or lower alkyl with the proviso that at least one of $R^3$, $R^4$ and $R^5$ is lower alkyl;
and $R^6$ and $R^7$ each represent hydrogen or lower alkyl which possess anti-ulcer activity.

17 Claims, No Drawings

8-BENZYLIDENE-5,6,7,8-TETRAHYDROQUINOLINE DERIVATIVES

This invention relates to heterocyclic compounds, more particularly to 5,6,7,8-tetrahydroquinolines, processes for their preparation and pharmaceutical compositions containing them.

8-Benzylidene-5,6,7,8-tetrahydroquinolines have been described in the literature—see for example Chemical Abstracts, Volume 73, 87755d and Arch. Pharm. (Weinheim), 1980, 313, pps 826–832 by E. Reimann and co-workers. However no pharmaceutical activity is disclosed.

We have now found a novel series of 8-benzylidene-5,6,7,8-tetrahydroquinolines which possess pharmaceutical activity and in some instances are also useful as intermediates to other compounds in the series.

Accordingly this invention provides compounds of formula

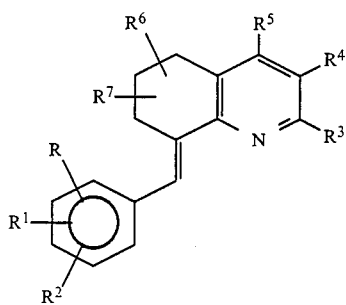

wherein

R represents alkoxy, alkanoyloxy or hydroxy, $R^1$ and $R^2$ independently represent hydrogen, alkoxy, alkanoyloxy, hydroxy or alkyl;

$R^3$, $R^4$ and $R^5$ each represent hydrogen or alkyl with the proviso that at least one of $R^3$, $R^4$ and $R^5$ is alkyl;

and $R^6$ and $R^7$ each represent hydrogen or alkyl; and acid addition salts thereof.

Examples of alkyl or alkoxy groups include such groups containing 1 to 6 carbon atoms, preferably 1 to 4 carbon atoms e.g. methyl, methoxy, ethyl, ethoxy, n-propyl, n-propoxy, etc.

Alkanoyloxy groups preferably have 2 to 7 carbon atoms, e.g. acetyloxy, propionyloxy, butyryloxy, etc.

Examples of each of $R^3$, $R^4$ and $R^5$ are methyl, ethyl, propyl. Preferably $R^3$ is hydrogen, most preferably $R^3$ and $R^5$ or $R^3$ and $R^4$ are both hydrogen. Examples of $R^6$ and $R^7$ are methyl, ethyl, propyl.

Examples of groups for R are hydroxy, methoxy, ethoxy, n-propoxy, isopropoxy, acetoxy, propionyloxy and butyryloxy.

Examples of groups for $R^1$ or $R^2$ are methyl, ethyl, propyl, methoxy, ethoxy, propoxy, acetoxy, propionyloxy, butyryloxy and hydroxy.

When $R^2$ is hydrogen examples of R and $R^1$ are respectively acetoxy, acetoxy; hydroxy, hydroxy; acetoxy, methoxy and methoxy, hydroxy.

Preferably R and $R^1$ represent one of the following: 3,4-diacetoxy; 3,4-dihydroxy; 3-acetoxy-4-methoxy; 3-hydroxy-4-methoxy; 3-methoxy-4-hydroxy; 2-hydroxy-3-methoxy, when $R^1$ and $R^2$ are both hydrogen R is preferably 2-methoxy, 2,3 or 4-acetoxy or 3-hydroxy.

The compounds of formula I form salts with inorganic or organic acids. Examples of acid addition salts are those formed with one of the following: hydrochloric, hydrobromic, hydroiodic, sulphuric, nitric, phosphoric, methanesulphonic, acetic, maleic, citric, fumaric, tartaric, malonic or formic acids.

The compounds of formula I possess anti-ulcer activity as measured by a standard test procedure and accordingly are useful for the treatment of ulcers in mammals.

Anti-ulcer activity was determined by the stress-induced erosion test of Senay and Levine, Proc. Soc. Exp. Biol. Med., 124, 1221–3 (1967). The procedure used was as follows.

Male rats, weighing between 80 and 120 gms. were fasted overnight with water ad lib. The rats were then divided into groups of six and dosed orally with the test drug in the form of a solution or with the vehicle alone, 0.5% carboxymethylcellulose, in a volume of 10 ml/kg. After 30 minutes the rats were inserted into aluminium restraining tubes measuring 1⅝ inches in diameter by 5 inches and placed in the cold (4±1° C.) for 3 hours. Immediately after cold exposure the rats were killed with intracranial alcohol and their stomachs excised and opened along the greater curvature. Each stomach was washed gently free of contents with warm tap water and pinned out on a board. The condition of the gastric mucosa was then scored from 0 to 6 on the following scale:

| Ulcers | | | |
|---|---|---|---|
| 0–6 | 0 | = | No ulcers |
| | 1 | = | Pin point haemorrhagic site |
| | 2 | ⎫ | Several discrete pin point |
| | 3 | ⎬ = | haemorrhagic sites |
| | 4 | ⎫ | Large eroded sites with |
| | 5 | ⎬ = | |
| | 6 | ⎭ | haemorrhage |

The maximum possible score for each animal was 6 and for the group 36. Decrease in ulcer formation was calculated as a percentage of the control score, i.e.

$$\text{Percentage Inhibition} = \frac{\text{Mean Control group score} - \text{Mean Test group score}}{\text{Mean Control group score}} \times 100$$

The statistical significance of the effect is assessed by Student's t-test. Experience has shown that +45% inhibition may be taken as a threshold value below which compounds can be regarded as inactive or not sufficiently active to be considered further.

In the above mentioned test the following representative compounds of formula I were particularly active giving results as shown:

| | Dose (mg/kg) | Inhibition |
|---|---|---|
| E-8-(3,4-Diacetoxybenzylidene)-5,6,7,8-tetrahydro-3-methylquinoline | 100 | 93% |
| | 30 | 67% |
| | 10 | 40% |
| E-8-(2-Methoxybenzylidene)-5,6,7,8-tetrahydro-3-methylquinoline | 100 | 87% |
| | 30 | 21% |
| E-5,6,7,8-Tetrahydro-8-(4-hydroxy-3-methoxybenzylidene)-3-methylquinoline | 100 | 66% |
| | 30 | 60% |
| | 10 | 33% |

This invention also provides processes for preparing the compounds of formula I or acid addition salts thereof.

Accordingly a first process for preparing compounds of formula I comprises dehydrating a compound of formula

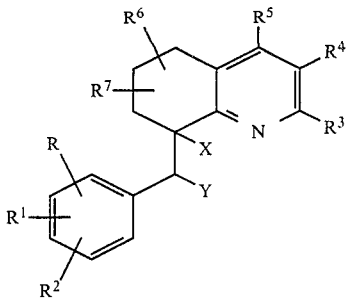

(II)

wherein one of X and Y is hydroxy, the remaining one of X and Y being hydrogen; R, $R^1$, $R^2$, $R^3$, $R^4$, $R^5$, $R^6$ and $R^7$ are as defined above, R, $R^1$ and $R^2$ each also represent hydroxy groups protected by a protecting group and removing any protecting group.

The dehydration may be carried out with usual dehydrating agents, e.g. polyphosphoric acid or with an organic acid anhydride, e.g. acetic anhydride, (in which case an acetylated derivative may be formed, from which acetic acid is eliminated to give the compound of formula I). Use of an acid anhydride to effect dehydration may also acylate any R, $R^1$ or $R^2$ hydroxy groups in which case hydrolysis may be used if desired as an after process to revert to hydroxy substituents. Also if desired any hydroxy substituents in the compound of formula II may be protected by any group known in the art for protecting hydroxy groups and then removing such protecting groups.

In this connection attention is directed to well known textbooks on peptide chemistry which illustrate such hydroxy protecting groups and methods for their removal—see for example E. Schroder and K. Lubke, "The Peptides", Volume 1, Academic Press, New York and London, 1965.

The compounds of formula II wherein X is H and Y is OH may be prepared by treatment of a compound of formula III

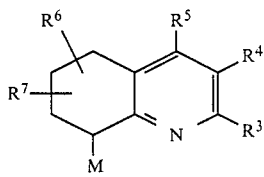

(III)

wherein $R^3$, $R^4$, $R^5$, $R^6$ and $R^7$ are as defined in connection with formula I, and M is hydrogen, an alkali metal (e.g. sodium, potassium or lithium) or MgHal, where Hal is chlorine, bromine or iodine, with an aldehyde of formula IV

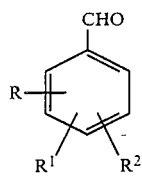

(IV)

wherein R, $R^1$ and $R^2$ are as defined in connection with formula II, if necessary (e.g. when M is an alkali metal) followed by treatment with a proton source, e.g. dilute acid.

When M is hydrogen the reaction may be carried out at room temperature or below in a suitable solvent, e.g. acetic acid and/or in the presence of a Lewis acid e.g. zinc chloride. If the aldehyde of formula IV and the tetrahydroquinoline of formula III (wherein M is H) are reacted simultaneously under dehydrating conditions then it is possible to produce the compounds of formula I directly without isolation of an intermediate hydroxy compound of formula II wherein X is H and Y is OH. Examples of suitable conditions for effecting such a reaction are the presence of a dehydrating agent such as an organic acid anhydride (including mixed anhydrides) e.g. acetic anhydride preferably at elevated temperature. Polyphosphoric acid or the like may also be used as the dehydrating agent. Hydroxy substituent groups may be protected in similar manner to that described in connection with the dehydration of compounds of formula II described above.

Accordingly this invention also provides a process for preparing a compound of formula I as hereinbefore defined which comprises reacting a compound of formula III wherein M is hydrogen with an aldehyde of formula IV as hereinbefore defined under dehydrating conditions, and if required removing one or more hydroxy protecting groups.

Compounds of formula II wherein X is OH and Y is hydrogen may be prepared by reacting a compound of formula

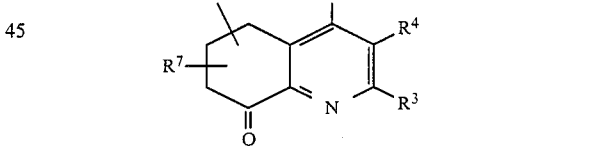

(V)

wherein $R^3$, $R^4$, $R^5$, $R^6$ and $R^7$ are as hereinbefore defined with a compound of formula

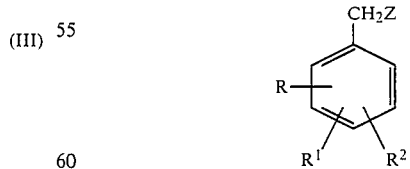

(VI)

wherein R, $R^1$ and $R^2$ are as hereinbefore defined in connection with formula II and Z is an alkali metal or MgHal where Hal is chlorine, bromine or iodine, followed by treatment with a proton source, e.g. dilute acid.

A further process for preparing compounds of formula I employs the Peterson reaction (J. Organic Chem.

1968, 780; Carey and Toler ibid, 1976, 41, 1966, Hudrik & Peterson J. Amer. Chem. Soc. 1975, 97, 1464)—see the scheme below

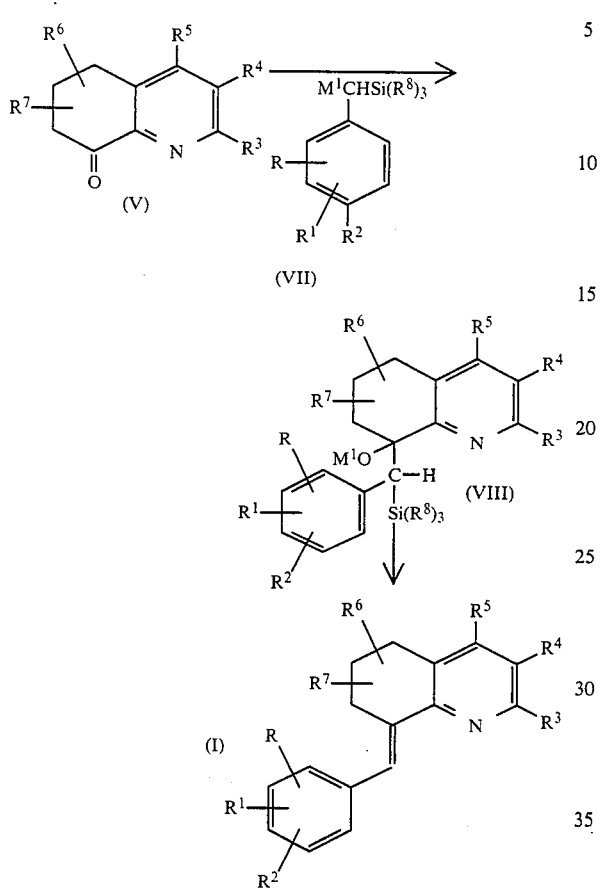

The process comprises reacting a compound of formula V as defined above with a silicon compound of formula VII wherein R, $R^1$ and $R^2$ are as defined above, $M^1$ is an alkali metal especially lithium or MgHal where Hal is chlorine, bromine or iodine and $(R^8)_3$ represents three $R^8$ radicals the same or different selected from alkyl, cycloalkyl, aralkyl, aryl or electron donating substituents such as alkoxy, cycloalkoxy, aralkoxy, aryloxy, alkylthio, cycloalkylthio, aralkylthio or arylthio, the group $R^bR^cN$— wherein $R^b$ and $R^c$ are selected from alkyl, cycloalkyl, aryl and aralkyl or $R^b$ and $R^c$ may be joined to form a heterocyclic ring with the nitrogen atom (e.g. a piperidinyl or pyrrolidinyl ring, which may be substituted e.g. by alkyl), to give a silyl compound VIII which is treated under acidic or basic conditions to give compound I. If the conditions of work up are acidic (e.g. sulphuric acid or trifluoroacetic acid) then compound VIII will usually be converted first into a compound VIII where $M^1$ is H, but basic conditions (e.g. sodium or potassium hydride) and use of fluoride ions (e.g. KF or LiF) usually result in direct formation of compound I. As before protecting groups for hydroxy substituents are removed as required.

Preferably $R^8$ in the compound of formula VII is an alkyl radical of 1 to 6 carbon atoms, most preferably methyl, or an aryl radical, most preferably phenyl.

The silicon compound VII starting materials may be prepared from corresponding compounds of formula

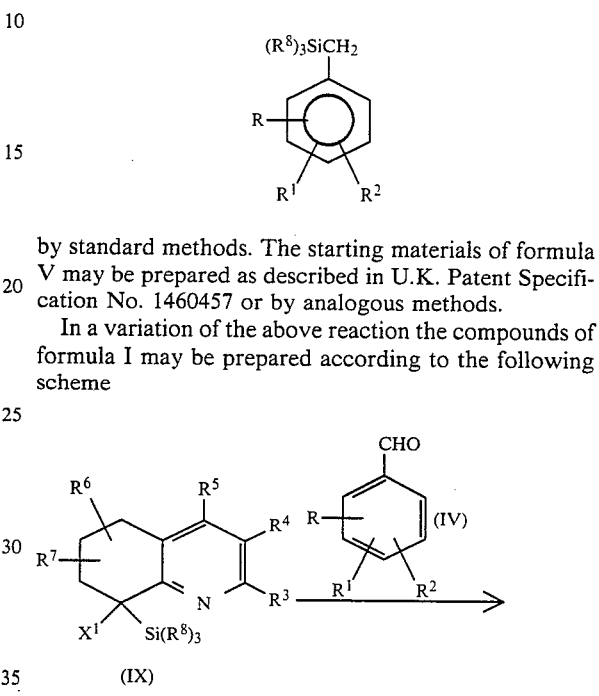

by standard methods. The starting materials of formula V may be prepared as described in U.K. Patent Specification No. 1460457 or by analogous methods.

In a variation of the above reaction the compounds of formula I may be prepared according to the following scheme

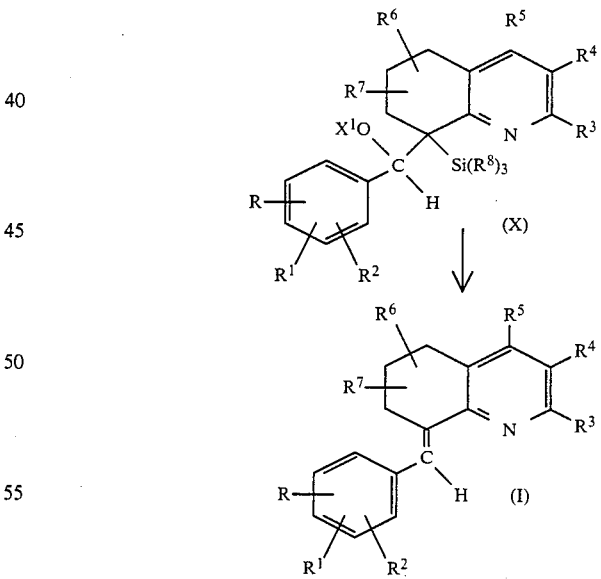

A silicon compound of formula IX, where $R^3$, $R^4$, $R^5$, $R^6$, $R^7$ and $R^8$ are as previously defined in connection with formula V and $X^1$ is hydrogen, sodium, potassium or lithium is reacted with an aldehyde compound of formula IV as hereinbefore defined to obtain a silyl intermediate of formula X which is converted to compound I by acid or base treatment as described for the previous reaction scheme, and removing any protecting groups as required. The starting compound IX may be prepared as described in our U.K. Patent Application 8218466 (H-325p) filed 25th June 1982, or by analogous methods. Briefly a compound of formula

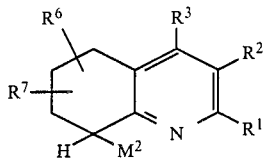

(XI)

where $M^2$ is sodium, potassium or lithium is treated with a silylating agent of formula $(R^8)_3SiHal$ where $R^8$ is as defined above and Hal is chlorine, bromine or iodine, to obtain a compound of formula IX wherein $X^1$ is hydrogen and if desired treating this with a metal compound $R^*M^2$ where $M^2$ is sodium, potassium or lithium and $R^*$ is alkyl, cycloalkyl, aralkyl or aryl or an amine residue to obtain a compound of formula IX where $X^1$ is sodium, potassium or lithium.

Alternatively compounds of formula I may be prepared by the Wittig reaction (see Peterson loc cit for reference thereto) according to the scheme below

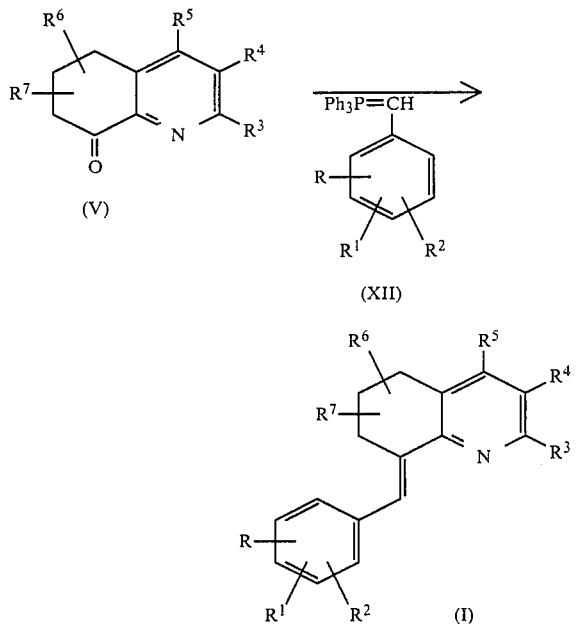

in which formulae $R^1$, $R^2$, $R^3$, $R^4$, $R^5$, $R^6$ and $R^7$ are as defined in connection with the previous reaction scheme, and removing any hydroxy protecting groups as required.

The Wittig phosphorus reagent of formula XII used in this reaction may be prepared by reacting $Ph_3P$ with an appropriate compound of formula

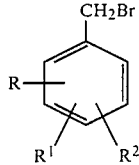

(XIII)

followed by reaction with a suitable base.

Once a compound of formula I is prepared in which any of R, $R^1$ and $R^2$ is alkanoyloxy then such compounds may be hydrolysed to give corresponding hydroxy compounds of formula I. Similarly compounds of formula I wherein any of R, $R^1$ and $R^2$ is hydroxy may be acylated, e.g. using alkanoyl halides to give corresponding alkanoyl compounds of formula I. When any of R, $R^1$ and $R^2$ is alkoxy then such compounds may be dealkylated using standard procedures to give corresponding hydroxy compounds of formula I. Accordingly compounds of formula I are intermediates for other compounds of formula I.

In any of the aforementioned reactions compounds of formula I may be isolated in free base form or as acid addition salts as desired.

The compounds of formula I and their acid addition salts may be used in pharmaceutical compositions.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more, e.g. 25 mg to 250 mg, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

In another aspect the invention provides as an anti-ulcer agent a compound of formula I or an acid addition salt thereof as defined above.

The following examples illustrate the invention:

EXAMPLE 1

E-8-(4-Acetoxy-3-methoxybenzylidene)-5,6,7,8-tetrahydro-4-methylquinoline

A mixture of 5,6,7,8-tetrahydro-4-methylquinoline (5.2 g), vanillin (5.37 g), zinc chloride (0.3 g) and acetic anhydride (50 ml) were refluxed under nitrogen for 16 hours. The solvent was removed by evaporation and the resulting residue was neutralised ($Na_2CO_3$) in the presence of ethyl acetate and was then extracted with ethyl acetate.

The ethyl acetate solution was extracted with 2N HCl and this extract was washed with ethyl acetate, basified ($Na_2CO_3$) and the product extracted with ethyl acetate. The ethyl acetate solution was dried ($MgSO_4$) and evaporated. The resulting residue was repeatedly extracted with hot hexane and the extracts allowed to cool. The resulting white solid was filtered, washed with cold hexane and finally dried to give the title compound (3.3 g). m.p. 110°–112° C.

Analysis: Found: C, 74.7; H, 6.95; N, 4.4%. $C_{20}H_{21}NO_3$ requires C, 74.3; H, 6.55; N, 4.3%.

EXAMPLE 2

E-5,6,7,8-Tetrahydro-8-[4-hydroxy-3-methoxybenzylidene]-4-methylquinoline

E-8-(4-Acetoxy-3-methoxybenzylidene)-5,6,7,8-tetrahydro-4-methylquinoline, HCl (from Example 1) (1.3 g) was dissolved in 2N HCl (20 ml) and heated at 90° C. for 4 hours. The resulting red solid was removed by filtration, washed with a small amount of ether and finally dried to give the title compound as the hydrochloride salt (1.15 g) m.p. 285°–287° C.

Analysis: Found: C, 67.6; H, 6.4; N, 4.3%. $C_{18}H_{19}NO_2HCl$ requires C, 68.0; H, 6.3; N, 4.4%.

EXAMPLE 3

E-8-(3,4-Diacetoxybenzylidene)-5,6,7,8-tetrahydro-4-methylquinoline

A mixture of 5,6,7,8-tetrahydro-4-methylquinoline (5.2 g), 3,4-dihydroxybenzaldehyde (4.88 g), zinc chloride (0.3 g) and acetic anhydride (50 ml) were refluxed under nitrogen for 16 hours.

The solvent was removed by evaporation and the resulting residue was neutralised ($Na_2CO_3$) in the presence of ethyl acetate and was then extracted with ethyl acetate. The ethyl acetate solution was extracted with 2N HCl and this extract was washed with ethyl acetate, basified ($Na_2CO_3$) and the product extracted with ethyl acetate. The ethyl acetate solution was dried ($MgSO_4$) and evaporated. The resulting residue was repeatedly extracted with hot hexane and then extracts allowed to cool giving a white solid.

This was filtered, washed with cold hexane and dried to give the title compound as the quarterhydrate (2.6 g). m.p. 126°–128° C.

Analysis: Found: C, 71.0; H, 6.2; N, 3.95%. $C_{21}H_{21}NO_4 \cdot \frac{1}{4}H_2O$ requires C, 70.9; H, 6.1; N, 3.9%.

EXAMPLE 4

E-5,6,7,8-Tetrahydro-8-[3,4-dihydroxybenzylidene]-4-methylquinoline

E-8-(4-Acetoxy-3-methoxybenzylidene)-5,6,7,8-tetrahydro-4-methylquinoline, HCl (1.0 g) (from Example 1) was dissolved in 2N HCl (20 ml) and heated at 90° C. for 4 hours. The resulting red solid was removed by filtration, washed with a small amount of ether and finally dried to give the title compound as the hydrochloride quarterhydrate salt (0.75 g), m.p. 278°–280° C.

Analysis: Found: C, 65.9; H, 6.2; N, 4.7%. $C_{17}H_{17}NO_2 \cdot HCl \cdot \frac{1}{4}H_2O$ requires: C, 66.2; H, 6.05; N, 4.5%.

EXAMPLE 5

E-8-(3,4-Diacetoxybenzylidene)-5,6,7,8-tetrahydro-3-methylquinoline

A mixture of 5,6,7,8-tetrahydro-3-methylquinoline (20 ml), 3,4-dihydroxybenzaldehyde (20 g) and acetic anhydride (50 ml) was heated at 100° for 48 hours. Further acetic anhydride (50 ml) and $ZnCl_2$ (1 g) were added and the mixture was heated at reflux for 16 hours. The solvent was removed by evaporation, the residue was neutralised ($Na_2CO_3$) in the presence of ethyl acetate and extracted with ethyl acetate. The ethyl acetate solution was extracted with 2N HCl and this extract was washed with ethyl acetate, basified ($Na_2CO_3$) and extracted with $Et_2O$. The ether solution was dried ($MgSO_4$) and evaporated and the residue triturated with hexane and recrystallised from di-isopropyl ether to give the title compound (22 g) m.p. 100°–1° C.

Analysis: Found: C, 71.85; H, 5.9; N, 3.9%. $C_{21}H_{21}NO_4$ requires C, 71.8; H, 6.0; N, 4.0%.

EXAMPLE 6

E-5,6,7,8-tetrahydro-8-(3,4-dihydroxybenzylidene)-3-methylquinoline

A solution of E-8-(3,4-diacetoxybenzylidene)-5,6,7,8-tetrahydro-3-methylquinoline (prepared according to Example 5) (3 g) in 2N HCl (50 ml) was heated at 80° for 1¾ hours. The precipitated crystals were removed by filtration and dried to give the title compound as the hydrochloride, quarterhydrate (2.6 g) m.p. 265° C. decomp.

Analysis: Found: C, 66.1; H, 6.4; N, 4.4%. $C_{17}H_{17}NO_2 \cdot HCl \cdot \frac{1}{4}H_2O$ requires C, 66.2; H, 6.0; N, 4.5%.

EXAMPLE 7

E-8-(2-Acetoxybenzylidene)-5,6,7,8-tetrahydro-3-methylquinoline

A mixture of 5,6,7,8-tetrahydro-3-methylquinoline (20 ml), salicylaldehyde (20 ml) and acetic anhydride (40 ml) was heated at 100° for 48 hours. Further acetic anhydride (50 ml) and $ZnCl_2$ (1 g) was added and the mixture was heated at reflux for 16 hours. The solvent was removed by evaporation and the residue was dissolved in ethyl acetate, neutralised with $Na_2CO_3$ solution and extracted with ethyl acetate. The extracts were extracted with 2N HCl and the extract washed with ethyl acetate basified (Na$_2$CO$_3$) and extracted with diethyl ether. The solution was dried (MgSO$_4$) and evaporated to give an oil which was triturated with n-hexane and recrystallised from n-hexane to give the title compound (12 g) m.p. 85°–7° C.

Analysis: Found: C, 78.1; H, 6.5; N, 4.5%. C$_{19}$H$_{19}$NO$_2$ requires: C, 77.8; H, 6.5; N, 4.8%.

EXAMPLE 8

E-8-(4-Acetoxy-3-methoxybenzylidene)-5,6,7,8-tetrahydro-3-methylquinoline

A mixture of 5,6,7,8-tetrahydro-3-methylquinoline (20 ml), vanillin (25 g), acetic anhydride (50 ml), and zinc chloride (1 g) was heated at reflux for 30 hours. The solvent was removed by evaporation and the residue was dissolved in ethyl acetate. This solution was shaken with 2N HCl and a crystalline solid was deposited. This was removed by filtration, washed with diethyl ether and propan-2-ol/diethyl ether. The product was then dried to give the title compound as the hydrochloride salt (34 g) m.p. 223°–5° C.

Analysis: Found: C, 66.5; H, 6.1; N, 3.8%. C$_{20}$H$_{21}$NO$_3$.HCl requires C, 66.8; H, 6.2; N, 3.7%.

EXAMPLE 9

E-5,6,7,8-Tetrahydro-8-(4-hydroxy-3-methoxybenzylidene)-3-methylquinoline

A mixture of E-5,6,7,8-Tetrahydro-8-(4-acetoxy-3-methoxybenzylidene)-3-methylquinoline HCl (prepared according to Example 8) (3.0 g) and 2N HCl (50 ml) were heated for 1 hour on a steam bath. After cooling the yellow crystals were removed by filtration, washed with diethyl ether and then dried to give the title compound as the hydrochloride salt (2.5 g). m.p. 257°–60° C.

Analysis: Found C, 67.95; H, 6.6; N, 4.3%. C$_{18}$H$_{19}$NO$_2$.HCl requires C, 68.0; H, 6.3; N, 4.4%.

EXAMPLE 10

E-8-(3-Acetoxy-4-methoxybenzylidene)-5,6,7,8-tetrahydro-3-methylquinoline

A mixture of 5,6,7,8-tetrahydro-3-methylquinoline (20 ml), isovanillin (25 g), acetic anhydride (50 ml) and ZnCl$_2$ (1 g) was heated at reflux for 17 hours. The solvent was removed by evaporation and the residue dissolved in ethyl acetate. The solution was acidified with 2N HCl, a yellow solid being obtained. This was washed with diethyl ether and then dried to give the title compound as the hydrochloride, sesquihydrate (33 g) m.p. 222°–4° C.

Analysis: Found: C, 62.0; H, 6.1; N, 3.7%. C$_{20}$H$_{21}$NO$_3$.HCl.1½H$_2$O requires C, 62.1; H, 6.25; N, 3.6.

EXAMPLE 11

E-5,6,7,8-Tetrahydro-8-(3-hydroxy-4-methoxybenzylidene)-3-methylquinoline

E-8-(3-Acetoxy-4-methoxybenzylidene)-5,6,7,8-tetrahydro-3-methylquinoline (prepared according to Example 10) (3 g) in 2N HCl (50 ml) was heated at 80° C. for 1 hour. The resulting yellow solid was removed by filtration and washed with diethyl ether and hexane and dried to obtain the title compound as the hydrochloride, quarterhydrate salt (2.2 g). m.p. 233°–5° C.

Analysis: Found: C, 66.7; H, 6.3; N, 4.3%. C$_{18}$H$_{19}$NO$_2$.HCl.¼H$_2$O requires, C, 67.1; H, 6.4; N, 4.3%.

EXAMPLE 12

E-8-(2-Methoxybenzylidene)-5,6,7,8-tetrahydro-3-methylquinoline 5,6,7,8-Tetrahydro-3-methylquinoline (6.6 g) was added to o-anisaldehyde (8.16 g) in acetic anhydride (10 ml) and was heated to reflux for 14 hours after which the solvent was removed under reduced pressure. The residue was dissolved in ethyl acetate (50 ml) and was added to 2N HCl (150 ml), the aqueous layer was basified (Na$_2$CO$_3$) and extracted with ethyl acetate (4×100 ml) dried (MgSO$_4$) and evaporated under reduced pressure. The residue was washed with several aliquots of hot hexane and was then dissolved in a small volume of boiling propan-2-ol and etherial hydrogen chloride was added in excess. On cooling a precipitate formed and was removed by filtration, washed with ether and dried under vacuum to give the title compound as the hydrochloride salt (2.6 g) m.p. 221°–222.5° C.

Analysis: Found: C, 71.5; H, 6.6; N, 4.5%. C$_{18}$H$_{19}$NO.HCl requires C, 71.6; H, 6.7; N, 4.6%.

EXAMPLE 13

E-8-(2-Hydroxy-3-methoxybenzylidene)-5,6,7,8-tetrahydro-3-methylquinoline 5,6,7,8-Tetrahydro-3-methylquinoline (20 ml), o-vanillin (25 g), acetic anhydride (50 ml), and ZnCl$_2$ (1 g) were heated at reflux for 17 hours. The solvent was removed by evaporation and the residue was dissolved in ethyl acetate (100 ml) and acidified with 2N HCl solution. The solid obtained was removed by filtration and the aqueous layer was basified with Na$_2$CO$_3$ and shaken with diethyl ether. A solid was obtained in the ether layer which was removed by filtration. The combined solids were dissolved in 1N sodium hydroxide and the solution was extracted with ethyl acetate. The extracts were dried over MgSO$_4$ and the solvent was removed by evaporation. The crystals obtained were washed with hexane and dried to give the title compound (6 g) m.p. 149°–153° C.

Analysis: Found: C, 76.7; H, 6.8; N, 5.0%. C$_{18}$H$_{18}$NO$_2$ requires C, 77.1; H, 6.5; N, 5.0%.

EXAMPLE 14

E-8-(3-Acetoxybenzylidene)-5,6,7,8-tetrahydro-3-methylquinoline

A mixture of 5,6,7,8-tetrahydro-3-methylquinoline (20 ml), m-hydroxybenzaldehyde (20 g), acetic anhydride (50 ml) and ZnCl$_2$ (1 g) was heated at reflux for 3½ hours. The solvent was removed by evaporation and the residue dissolved in ethyl acetate (300 ml). The solution was extracted with 2N HCl, and the acidic phase was washed once with ethyl acetate. It was then basified (Na$_2$CO$_3$) and the product extracted into a mixture of diethyl ether and ethyl acetate. The solvent was removed by evaporation and the residue crystallised from di-isopropyl ether, washed twice with hexane and then dried to give the title compound as the hemihydrate (7.4 g). m.p. 66°–8° C.

Analysis: Found: C, 75.7; H, 6.5; N, 4.6%. C$_{19}$H$_{19}$NO$_2$.½H$_2$O requires C, 75.5; H, 6.7; N, 4.6%.

EXAMPLE 15

E-5,6,7,8-Tetrahydro-8-(3-hydroxybenzylidene)-3-methylquinoline

The product of Example 14, E-8-(3-Acetoxybenzylidene)-5,6,7,8-tetrahydro-3-methylquinoline (3 g) in 2N HCl (50 ml) was heated at 80° C. for 1 hour. On cooling crystals were removed by filtration, washed with diethyl ether and dried to give the title compound as the hydrochloride salt (2.2 g). m.p. 264°–6° C.

Analysis: Found: C, 71.0; H, 6.3; N, 4.9%. $C_{17}H_{17}NO.HCl$ requires C, 70.95; H, 6.3; N, 4.9%.

EXAMPLE 16

E-8-(4-Acetoxybenzylidene)-5,6,7,8-tetrahydro-3-methylquinoline 5,6,7,8-Tetrahydro-3-methylquinoline (6.6 g) was dissolved in acetic anhydride (10 ml) and 4-hydroxybenzaldehyde (7.35 g) was added. The mixture was allowed to reflux for 18 hours after which the solvent was removed under reduced pressure. The residue was added to 1M NaOH (300 ml) and the solid extracted with dichloromethane (3×150 ml) and dried ($Na_2SO_4$). Solvent was removed under reduced pressure. The solid residue was recrystallised from ethyl acetate to give the title compound (4.5 g). m.p. 119°–122° C.

Analysis: Found: C, 78.0; H, 6.7; N, 4.7%. $C_{19}H_{19}NO_2$ requires C, 77.8; H, 6.5; N, 4.8%.

EXAMPLE 17

E-5,6,7,8-Tetrahydro-7-(4-hydroxybenzylidene)-3-methylquinoline

A mixture of 5,6,7,8-tetrahydro-3-methylquinoline (20 ml), p-hydroxybenzaldehyde (20 g), acetic anhydride (50 ml), and $ZnCl_2$ (1 g) was heated at reflux for 25 hours. The solvent was removed by evaporation and the residue dissolved in ethyl acetate. This solution was acidified with 2N HCl and a crystalline solid precipitated. The solid was removed by filtration, washed with diethyl ether and then dried to give the title compound as the hydrochloride, quarterhydrate (28 g), m.p. 265° C. decomp.

Analysis: Found: C, 69.85; H, 6.2; N, 4.8%. $C_{17}H_{17}NO.HCl.\frac{1}{4}H_2O$ requires C, 69.9; H, 6.4; N, 4.8%.

I claim:

1. A compound of formula

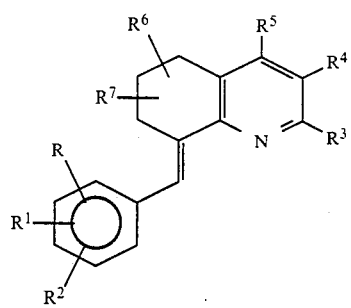

(I)

or a pharmaceutically acceptable acid addition salt thereof, wherein

R represents lower alkoxy, alkanoyloxy of 2 to 7 carbon atoms or hydroxy;

$R^1$ and $R^2$ independently represent hydrogen, lower alkoxy, alkanoyloxy of 2 to 7 carbon atoms, hydroxy or lower alkyl;

$R^3$, $R^4$ and $R^5$ each represent hydrogen or lower alkyl with the proviso that at least one of $R^3$, $R^4$ and $R^5$ is the lower alkyl;

and $R^6$ and $R^7$ each represent hydrogen or lower alkyl, providing that when one of $R^3$, $R^4$ and $R^5$ represents a tertiary alkyl group, the other two are hydrogen.

2. A compound of formula I as claimed in claim 1 wherein R represents hydroxy, methoxy, ethoxy, n-propoxy, isopropoxy, acetoxy, propionyloxy or butyryloxy.

3. A compound of formula I as claimed in claim 2 wherein $R^1$ and $R^2$ independently represent hydrogen, methyl, ethyl, propyl, methoxy, ethoxy, n-propoxy, acetoxy, propionyloxy, butryloxy and hydroxy.

4. A compound of formula I as claimed in claim 1 wherein $R^2$ is hydrogen and R and $R^1$ are both acetoxy; both hydroxy; or R is acetoxy and $R^1$ is methoxy; or R is methoxy and $R^1$ is hydroxy.

5. A compound of formula I as claimed in claim 1 wherein one of $R^3$, $R^4$ and $R^5$ is methyl, ethyl or n-propyl and the remainder are both hydrogen.

6. A compound as claimed in claim 1 which is E-5,6,7,8-tetrahydro-8-[3,4-dihydroxybenzylidene]-4-methylquinoline.

7. A compound as claimed in claim 1 which is E-8-(3,4-diacetoxybenzylidene)-5,6,7,8-tetrahydro-3-methylquinoline.

8. A compound as claimed in claim 1 which is E-8-(4-acetoxy-3-methoxybenzylidene)-5,6,7,8-tetrahydro-3-methylquinoline.

9. A compound as claimed in claim 1 which is E-5,6,7,8-tetrahydro-8-(3,4-dihydroxybenzylidene)-3-methylquinoline.

10. A compound as claimed in claim 1 which is E-5,6,7,8-tetrahydro-8-(4-hydroxy-3-methoxybenzylidene)-3-methylquinoline.

11. A compound as claimed in claim 1 which is E-5,6,7,8-tetrahydro-8-(3-hydroxy-4-methoxybenzylidene)-3-methylquinoline.

12. A compound as claimed in claim 1 which is E-8-(2-methoxybenzylidene)-5,6,7,8-tetrahydro-3-methylquinoline.

13. A compound as claimed in claim 1 which is E-8-(2-hydroxy-3-methoxybenzylidene)-5,6,7,8-tetrahydro-3-methylquinoline.

14. A compound as claimed in claim 1 which is E-8-(2-acetoxybenzylidene)-5,6,7,8-tetrahydro-3-methylquinoline.

15. A compound as claimed in claim 1 which is E-5,6,7,8-tetrahydro-8-(3-hydroxybenzylidene)-3-methylquinoline.

16. A compound as claimed in claim 1 which is E-8-(4-acetoxybenzylidene)-5,6,7,8-tetrahydro-3-methylquinoline.

17. A pharmaceutical composition comprising an amount effective for treating ulcers in a mammal in need thereof of a compound of formula I as claimed in claim 1 or a pharmaceutically acceptable acid addition salt thereof and a pharmaceutically acceptable carrier.

* * * * *